United States Patent [19]
Wikswo, Jr. et al.

[11] Patent Number: 5,572,123
[45] Date of Patent: Nov. 5, 1996

[54] APPARATUS AND METHOD FOR ON-LINE INSPECTION OF ELECTRICALLY CONDUCTIVE FOOD PRODUCTS USING LIQUID ELECTROLYTE

[75] Inventors: John P. Wikswo, Jr., Brentwood; Yu P. Ma; William G. Jenks, both of Nashville, all of Tenn.; Christopher G. Bublitz; Gour S. Choudhury, both of Kodiak, Ak.

[73] Assignees: University of Alaska, Fairbanks, Ak.; Vanderbilt University, Nashville, Tenn.

[21] Appl. No.: 477,602

[22] Filed: Jun. 7, 1995

[51] Int. Cl.$^6$ ................................................. G01R 33/00
[52] U.S. Cl. ........................... 324/263; 324/228; 324/693
[58] Field of Search ................................. 324/200, 201, 324/226, 228, 262, 263, 425, 692, 693

[56] References Cited

U.S. PATENT DOCUMENTS

| | | | |
|---|---|---|---|
| 3,735,247 | 5/1973 | Harker | 324/226 |
| 3,855,531 | 12/1974 | Fielibert et al. | 324/693 |
| 4,240,026 | 12/1980 | Murphy et al. | 324/425 |
| 5,109,196 | 4/1992 | Wikswo, Jr. et al. | 324/263 |
| 5,126,654 | 6/1992 | Murphy et al. | 324/71.2 |
| 5,289,123 | 2/1994 | Bublitz et al. | 324/263 |

OTHER PUBLICATIONS

*New Way of Body Composition Analysis Using Total Body Electrical Conductivity Methods;* Wojciech Piasecki, et al. Rev. Sci. Instrum. 66(4), Apr. 1995; pp. 3037–3041.

*Cold, Hard and Objective;* by Warren Kester; *Beef*, Dec. 1991; pp. 14–18.

*Electrical Properties of Agricultural Products–A Critical Review;* by Stuart O. Nelson; *Transactions of the ASAE;* 1973; pp. 384–400.

Primary Examiner—Sandra L. O'Shea
Assistant Examiner—Jay M. Patidar
Attorney, Agent, or Firm—Richard V. Westerhoff; Eckert Seamans Cherin & Mellott

[57] ABSTRACT

Inclusions such as encysted parasites and spoilage in food products such as fish fillets are detected by immersing the food products in a bath of an electrolyte, such as a saline solution, having substantially the same electrical conductivity as the uncontaminated food product. An electrical current passed through the electrolyte also passes through the food product. Perturbations in the resulting magnetic field produced by the discontinuities in conductivity at the boundaries of the inclusions or of the spoiled article which have substantially different conductivities from that of the electrolyte and unspoiled food products, provide an indication of the presence of the contamination. Production line inspection rates are achieved by conveying the food products through a container filled with electrolyte and past an array of stationary magnetometers. Perturbations in the magnetic field at the edges of the container are cancelled by directing the current which flows through the electrolyte in a first direction back over the container in the opposite direction through a cancelling conductor, while fields produced by the supply leads are cancelled by using coaxial cable.

17 Claims, 5 Drawing Sheets

APPARATUS AND METHOD FOR ON-LINE INSPECTION OF ELECTRICALLY CONDUCTIVE FOOD PRODUCTS USING LIQUID ELECTROLYTE

This invention was made with government support under grant number NA66D0046 from the National Oceanic and Atmospheric Administration (NOAA).

The United States government has certain rights in the invention.

BACKGROUND OF THE INVENTION

FIELD OF THE INVENTION

This invention relates to an apparatus and method for a non-destructive detection of defects in food products such as the presence of parasites and spoilage in fish, and particularly to such an apparatus and method which detects perturbations in the magnetic fields produced by electrical currents passed through the food products, preferably on a production line basis.

BACKGROUND INFORMATION

Inspection of food products for contamination rapidly and effectively on an on-line basis is a continuing challenge for the food industry. A particular problem is the detection of encysted parasites in fish during the processing of fish fillets. Parasite infestation renders the fish unmarketable for health and aesthetic reasons. Presently, the only commercial method for detecting parasites is canalling, which involves inspecting each fillet over an illuminated translucent surface. This process cannot detect parasites embedded deeper than 6 mm in fish muscle. In fact, research has shown that canalling removes only about 60% to 70% of nematodes present. In addition, candling is labor intensive, accounting for approximately 50% of production costs, and is the rate limiting step during white fish fillet production. Pre-freezing processing delays associated with canalling increase fillet exposure time to high temperature, producing a lower quality product through enhanced microbial growth and enzyme activity. Problems associated with candling are increased in remote areas and aboard factory vessels which have difficulty retaining the skilled workers required.

Various alternatives for detecting parasites in fish fillets have been investigated such as: laser canalling, ultraviolet light inspection, conventional X-ray detection, ultrasonic detection, scanning with a laser acoustic microscope, and the pulse-echo technique. The major problem in the application of all of these alternative techniques is the inability to distinguish parasites from the surrounding flesh, and none of these methods have proved successful due to low sensitivity, poor resolution, and slow through put. Thus far, no satisfactory alternative to candling has been found.

U.S. Pat. No. 5,289,123 describes a method for detecting parasites in fish fillets which relies upon the fact that the electrical conductivity of the inclusions is substantially different from the electrical conductivity of the fish flesh. An electrical current is passed longitudinally through the fillet. A magnetometer, preferably a Superconducting QUantum Interference Device (SQUID) is used to map the magnetic field associated with perturbations in this current distribution as the longitudinal current is deflected by the parasite-containing cyst. A pair of electrodes are applied directly to the fish fillet in order to inject the current. There are several limitations to this approach. It is necessary to apply electrodes to the fillet, the edges of the fillet produce substantial signals because of the discontinuity in electrical current tangential to the surface of the fillet, and the wires that are used to apply current to the fillet produce substantial magnetic fields. These limitations are not conducive to implementation of the technique for production line non-destructive testing for defects in food products such as fish fillets.

There is a need therefore for an improved method and apparatus for non-destructive detection of defects in food products.

In particular there is a need for such improved apparatus and method which can provide reliable detection of inclusions such as parasite-containing cysts in fish at reasonable production line rates.

There is an associated need for such an improved method and apparatus which does not require connection of electrodes directly to each food product to be tested.

SUMMARY OF THE INVENTION

These needs and others are satisfied by the invention which is directed to an apparatus and method for inspection of electrically conductive food products wherein the food product is immersed in a bath of liquid electrolyte, such as a saline solution, contained in a container having the electrodes permanently attached to opposite ends or sides of the container. The liquid electrolyte is selected to have an electrical conductivity which matches the average electrical conductivity of the electrically conductive food product, so that the boundary between regions carrying current and regions not carrying current is moved from the edge of the food product to the edge of the container. Importantly, since the electrodes do not have to be connected to the food product, the food products can be conveyed through the bath of liquid electrolyte in the container past a detection station to increase production rates. Preferably, the container has an inlet and an outlet with a lower center section which remains filled With electrolyte, and conveying means serially conveying food products into the inlet, through the center section where it is totally immersed in the liquid electrolyte, and out of the outlet. A magnetometer, such as a SQUID magnetometer, and preferably an array of SQUID magnetometers extending transversely to the path of the conveying means, scans the food product and detects the component of the magnetic field perpendicular to the plane of the current.

The current is injected, preferably at opposite ends of the container through spaced apart first and second electrodes immersed in the electrolyte to produce a distributed current in the electrolyte. While the edge effects of the container can be subtracted from the detected signal, preferably they are cancelled by providing a cancelling conductor which surrounds and extends along the center section of the container between the electrodes. Perturbations caused by the supply leads are similarly cancelled by use of a coaxial cable, one lead of which is connected to one electrode and the other lead of which is connected to the other electrode through the cancelling conductor.

Alternatively, the electrical current can be induced in the electrolyte and the food product as it passes through the electrolyte by a sheet inducer placed adjacent to the container and to which an alternating current is applied.

The invention is suitable for inspecting electrically conductive food products for defects such as inclusions and spoilage. The inclusions can include parasites and even foreign objects such as fish hooks. Furthermore, the inclusions can include any contaminations, body or structure having an electrical conductivity different from that of the surrounding flesh or structure. For instance, the invention can be used for sexing fish by detecting roe in the females.

BRIEF DESCRIPTION OF THE DRAWINGS

A full understanding of the invention can be gained from the following description of the preferred embodiments when read in conjunction with the accompanying drawings in which:

FIG. 5 is a vertical sectional view of a schematic representation of

DESCRIPTION OF THE PREFERRED EMBODIMENT

The present invention is an improvement over the technique described in U.S. Pat. No. 5,289,123 which is hereby incorporated by reference. The invention will be described as applied to the detection of cysts containing parasites, such as nematodes, in fish fillets; however, its application to other food products will become apparent to those skilled in the art. As mentioned above, the technique described in U.S. Pat. No. 5,289,123 requires the connection of a pair of electrodes to the fish fillet. This is not only tedious and time consuming, and therefore not conducive to high production rates, but it also produces large signals at the edges of the fillet and adjacent the leads supplying current to the fillet which can mask inclusions at those locations.

Figure 1:
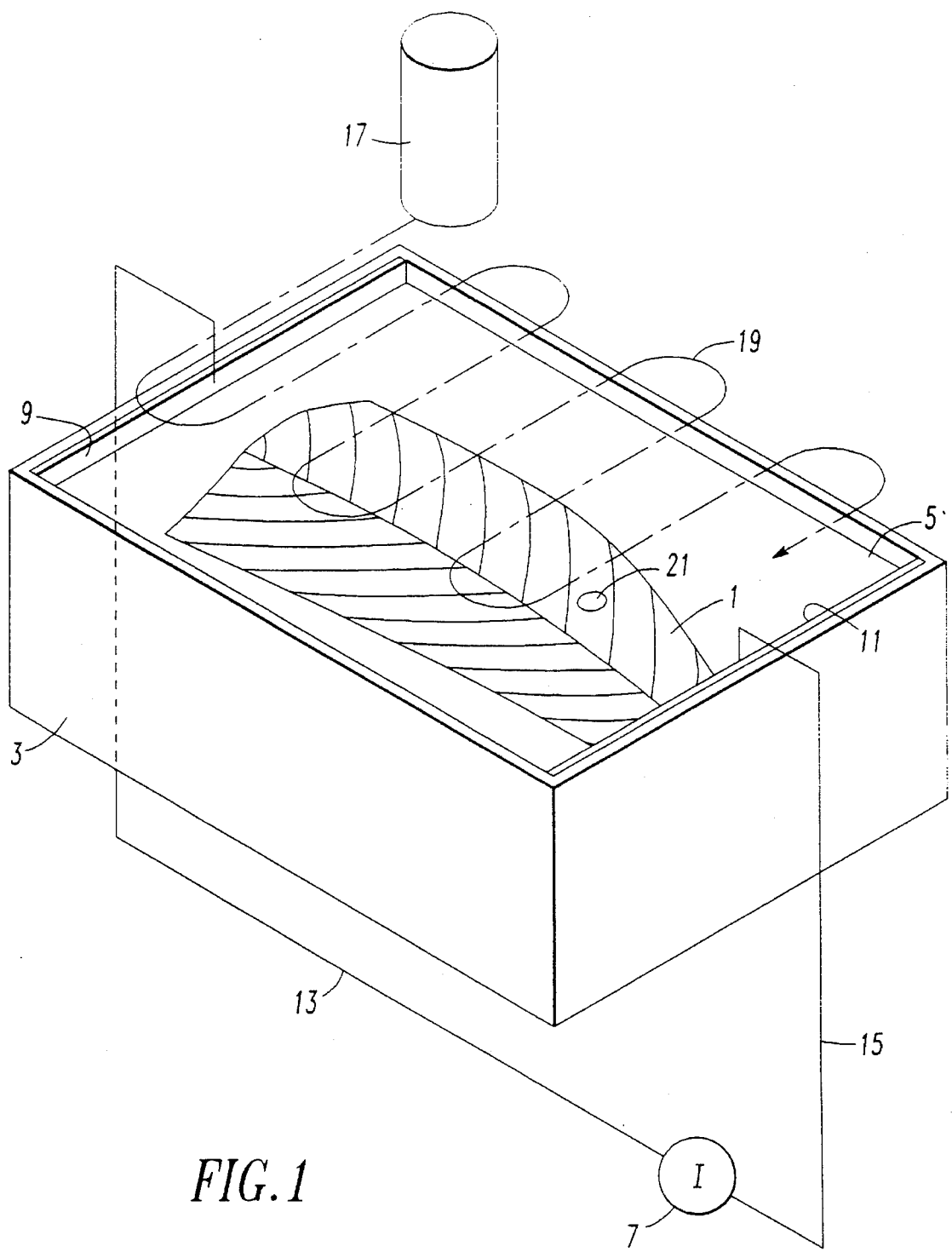
FIG. 1 is an isometric view of a basic embodiment of the invention.

In accordance with the present invention, and as shown in its simplest form in FIG. 1, the fish fillet 1 is placed in a container which is electrically non-conductive such as a glass dish 3. The dish 3 is filled with a liquid electrolyte 5, such as a saline solution, which has an electrical conductivity which substantially matches the average electrical conductivity of the fish flesh of the fillet 1. An electrical current I is produced in the saline solution 5 by an electrical power source 7 which is connected to a pair of electrodes 9 and 11 located on opposite ends of the glass dish 3 by leads 13 and 15, respectively. The electrodes 9 and 11 are conductive plates which extend across the respective ends of the glass dish 3 to thereby create a generally uniform distributed current I which flows through the electrolyte between the electrodes. This current I also flows through the fillet 1. Alternatively, the electrodes could be placed on opposite sides of the dish 3 rather than the ends, the essential feature being that the electrodes are positioned so that the current flowing between them passes through the fillet. A magnetometer 17, and preferably a Superconducting Quantum Interference Device (SQUID) magnetometer, is scanned over the top of the dish such as along the raster scan path 19. The planar current I produced by the spaced apart plate electrodes 9 and 11 generate a magnetic field, B, in a parallel plane. For an infinite plane, there is no component of the magnetic field perpendicular to these planes in the absence of anomalies in the electrical conductivity of the fish fillet. An inclusion 21 in the fish flesh such as a parasite-containing cyst causes perturbations in the current flow which produce a component of the magnetic field, $B_z$, perpendicular to the planar current which is detected by the magnetometer 17.

In the technique described in U.S. Pat. No. 5,289,123 wherein the fish fillet is not immersed in an electrolyte having a matching conductivity, the tangential currents at the boundaries of the fish fillet create sizable magnetic field components perpendicular to the plane of the current I which are detected by the magnetometer 17. In the present invention as shown in FIG. 1, because the dish is filled with saline solution 5 having an electrical conductivity which substantially matches the average electrical conductivity of the fillet 1, the boundary between regions carrying currents and regions not carrying currents is moved from the edge of the fillet to the edge of the dish. In addition, because the electrodes 9 and 11 are fixed to the dish, the geometry does not change in time and does not vary from fillet to fillet. Because the dish geometry remains fixed, it is possible to subtract the magnetic field associated with the edges of the dish and obtain a magnetic field map associated only with conductivity perturbations, such as those produced by a parasite-containing cyst 21. Furthermore, fish fillets 1 with abnormal electrical conductivities, perhaps through spoilage, will be evident because current will be displaced by the fillet-saline boundary and will produce a magnetic field components that can be detected by the SQUID magnetometer 17.

Even with the geometry of FIG. 1, there are still substantial magnetic fields produced by the current flowing in the wires 13 and 15 attached to the electrodes 9 and 11, and by the edges of the dish 3. It is, therefore, advantageous to eliminate the magnetic field from the dish itself and the wires. This is accomplished in the embodiment of the invention illustrated in FIG. 2. In this arrangement the sides, top and bottom surfaces of the insulative dish 23 are covered to form a closed chamber surrounding the dish by a thin electrically conducting layer 25. Electric current from the source 27 is supplied through a coaxial cable 29 having an inner conductor 31 and an outer conductor 33. The inner conductor 31 is connected to a first electrode 35 at one end of the dish 23, while the outer conductor 35 is connected to the electrically conductive layer 25 which in turn is connected to the second electrode 37 at the opposite end of the dish 23. Thus, the current I flows, for example, through the inner conductor 31 to the electrode 35, through the saline solution 5 and fish fillet 1 to the second electrode 37, back through the electrically conductive layer 25 to the outer coaxial conductor 33 and back to the source 27. In this arrangement, the magnetic field produced by the uniform current distribution within the chamber and that from current returning along the electrically conductive layer 25 partially cancel each other, so that the detected magnetic field will be produced primarily by deflected currents produced by conductivity anomalies within the dish 23. The cancellation will be perfect if the dish 23 is a cylinder whose axis 39 is parallel to the applied current I and the conductivity of the fillet I is both homogeneous and substantially matches that of the saline solution 5. Once the fillet 1 is placed in the dish, either through a removable top, side, bottom or end, the fish/dish combination can be scanned beneath a fixed magnetometer or a one-dimensional magnetometer array (i.e., a line of magnetometers), or the magnetometer 17 or magnetometer array can be scanned over the fillet 1. Alternatively, a two-dimensional magnetometer array or other magnetic imaging device could be used to map the magnetic field simultaneously over the entire fillet. Either ac or dc currents could be used. Because the electrical conductivity of skin on the fillet 1 will be different from that of the tissue, it is important that the skin of the fillet be placed adjacent to either the top or the bottom of the dish 23. The use of an enclosed dish also eliminates any magnetic noise due to waves in the surface of the liquid electrolyte 5 in the dish.

Figure 2:
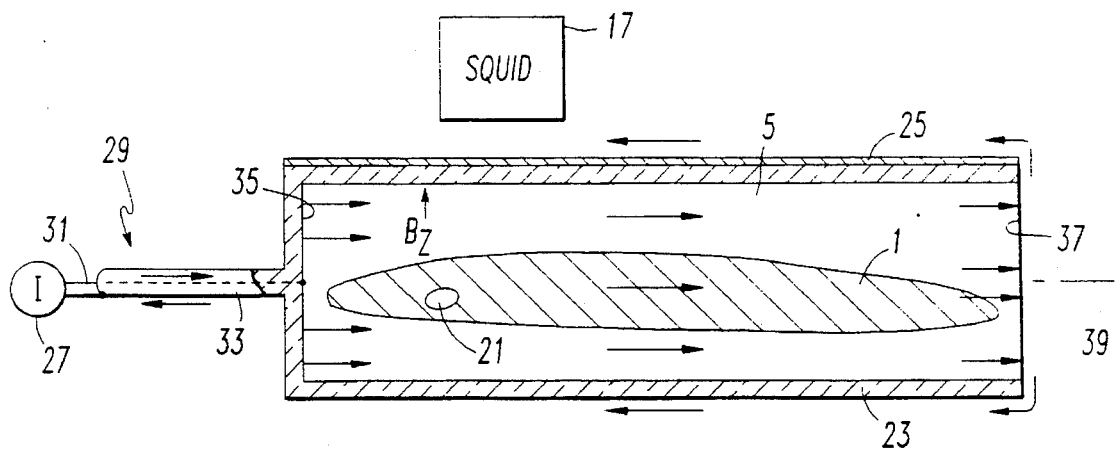
FIG. 2 is a vertical sectional view through a second embodiment of the invention.
Figure 3:
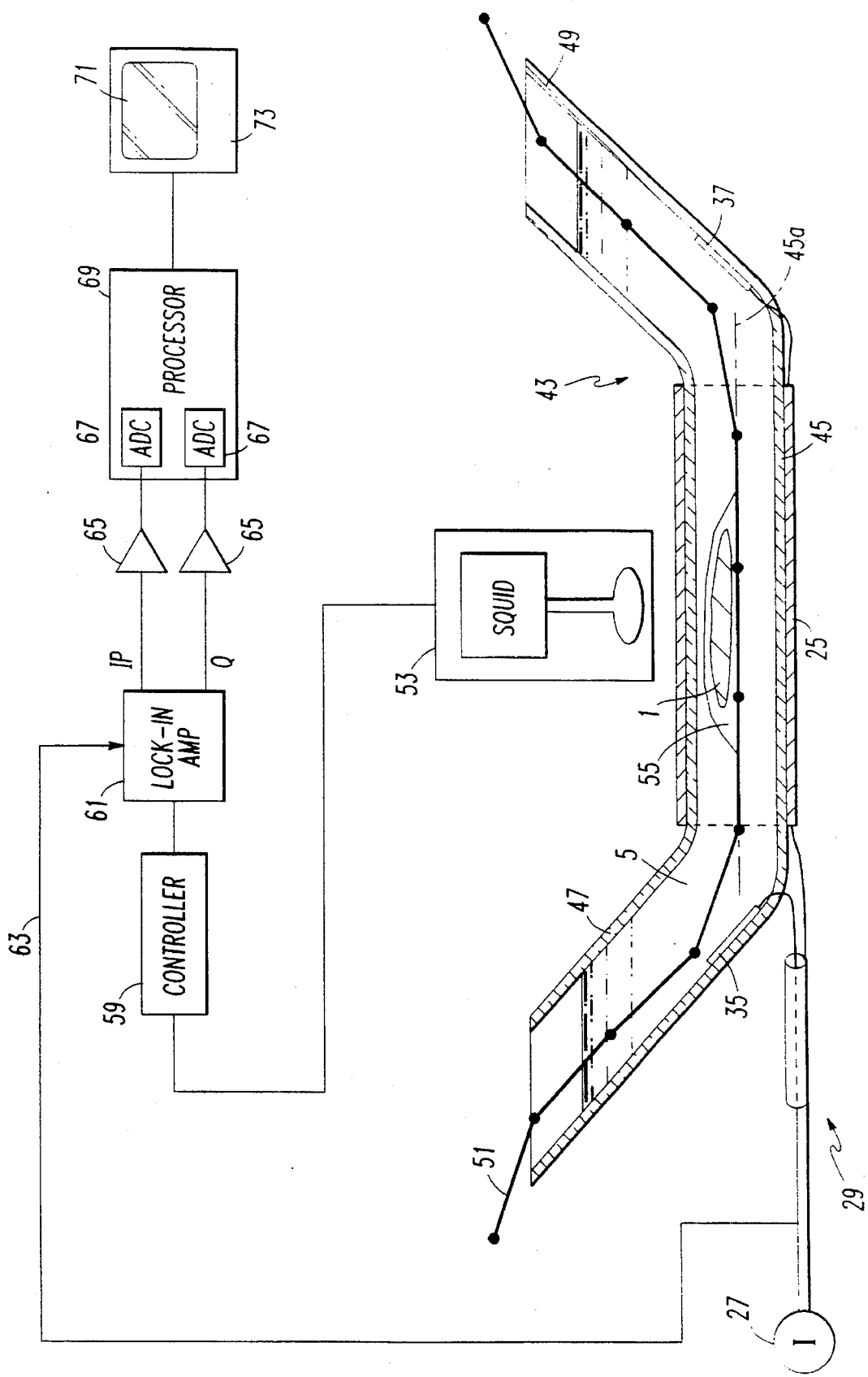
FIG. 3 is a vertical section through a schematic representation of a third embodiment of the invention suitable for use on a continuous production line and illustrating schematically in block form the electronics for the system.

One limitation of the approach illustrated in FIG. 2 is that the fillets must be individually placed in the electrically insulative dish 23. FIG. 3 shows an alternative configuration that will provide the same features as that shown in the embodiment of FIG. 2, but will be suitable for use in a continuous production line. In this geometry, an electrically insulative container 43 has a horizontally oriented, center section 45 forming a trough filled with the saline solution 5 and having a longitudinal axis 45a, an upwardly inclined inlet section 47 at one end of the center section 45, and an upwardly inclined outlet section 49 at the opposite end of the center section. The level of the saline solution 5 is maintained so that the center section 45 is always completely filled which eliminates waves in this section. An electrically insulative and non-magnetic conveyor belt 51 enters through the inlet section 47, passes through the center section 45 and exits through the outlet section 49 of the container 43. The conveyor belt 51 extends in a continuous loop (not shown). The fillets 1 are placed on the conveyer belt 51 and are drawn past the magnetometer 53 while submersed in the saline solution. The magnetometer 53 can include a one-dimensional array of magnetometers transverse to the plane of FIG. 3 so that the fillet is fully scanned as it passes the fixed magnetometer. As described in connection with FIG. 2, current from the source 27 is supplied through the coaxial cable 29 to a first electrode 35 at the inlet section 47 so that it flows through the saline solution and the food product to the second electrode 37 adjacent to the outlet section 49 of the container 43, and returns to the coaxial cable 29 through the cancelling conductor 25. A nylon cover net 55 or some other means can be used to keep the fillet 1 in place on the conveyor 51.

FIG. 3 also illustrates the electronic circuits which form part of the system for detecting inclusions in the fish fillet. The signals detected by the SQUID 53 are passed to a SQUID controller 59 which houses the circuit that maintains the SQUID sensor at its most sensitive values of operating parameters, insures that its sensitivity does not vary over time, and outputs a voltage proportional to the magnetic field the SQUID measures. Such controllers are known and commercially available units can readily be adapted to perform these functions. The processed signals are passed to a lock-in amplifier 61 which measures the amplitude of the detected signal at a particular phase relative to that of the applied current represented by a reference signal obtained from the current source 27 over the lead 63. The relative phase is represented by an in-phase signal IP and a quadrature signal Q each of which is passed through an amplifier 65 and digitized by an analog to digital converter (ADC) 67. The digitized component signals are processed by a digital processor 69 to generate a map which can be presented, for instance, on the monitor screen 71 of a personal computer 73. The arrangement shown in FIG. 3 is for ac currents injected into the fish fillet. For DC currents, the output of the SQUID controller 59 is applied directly to the ADC 67 for input to the digital processor 69.

As discussed, the magnetic fields could be detected by a variety of means, including, but not limited to, fluxgate magnetometers, Hall probe magnetometers, fiber optic magnetometers and magnetic optic crystals. The most sensitive magnetometer would utilize a Superconducting QUantum Interference Device (SQUID). The SQUIDs could be fabricated either from low transition temperature superconductors that operate in the vicinity of 4°K, or high transition-temperature materials that operate between 77° and 120°K. In most practical implementations of SQUID magnetometers, the SQUID sensor is connected to a superconducting magnetic flux transporter that is frequently configured as a differential magnetometer or gradiometer that rejects uniform fields such as those produced by distant noise sources. In the fish parasite detection system, a linear array of SQUID gradiometers could be placed either above or below the trough to allow rapid scanning of the fillet as it passes beneath the magnetometers.

Figure 4:
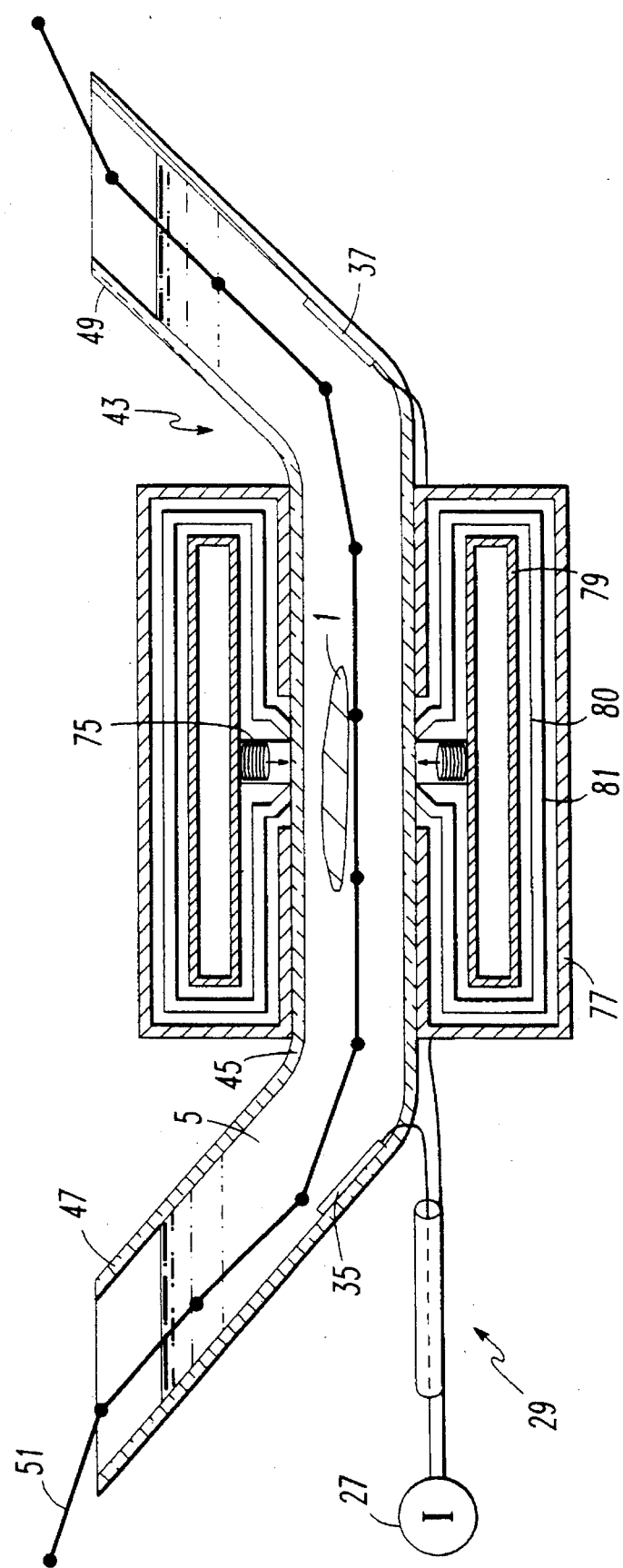
FIG. 4 is a vertical section illustrating yet another embodiment of the invention suitable for use in a magnetically noisy environment.

An advantage of utilizing superconductivity and cryogenics is that it is then possible to include in the system a superconducting magnetic shield that would virtually eliminate magnetic interference from the surrounding environment. An example of this geometry is shown in FIG. 4. In this configuration, a ring of SQUIDs 75 encircles the center section 45 of the container 43. The SQUIDs are housed in a dewar 77 which surrounds and extends along the center section 45 of the container. A superconducting shield 79 is mounted inside the dewar and filled with liquid helium. A 20°K thermal shield 80 and a 77°K thermal shield 81 are provided between the superconducting shield and the dewar wall. The magnetic shielding provided by this configuration would be sufficient to allow the device to be operated in a fish processing factory. The cryogenic environment required for the operation of the SQUID magnetometers and the magnetic shields can be provided by either liquid cryogens, a mechanical refrigerator or a combination of the two.

Figure 5:
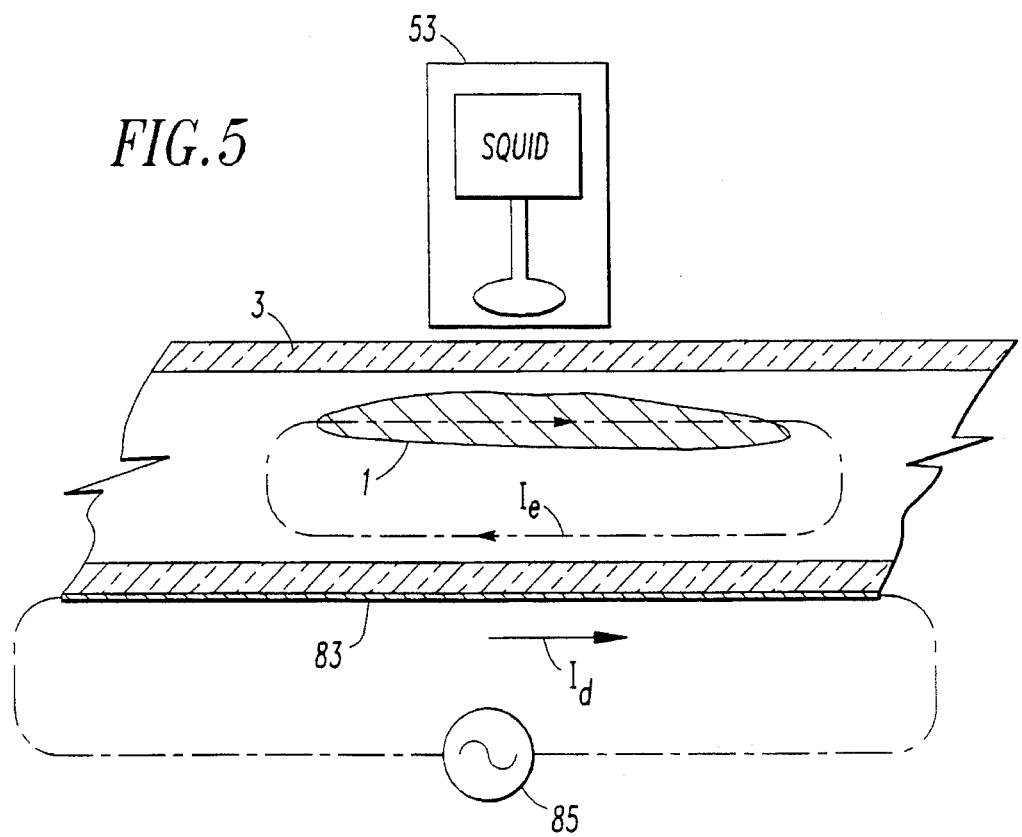

As an alternative to injecting electric current into the saline solution 5, an electrically-isolated sheet conductor 83 can be used to induce planar eddy currents $I_e$ in the dish 3 as shown in FIG. 5. Application of an alternating drive current $I_d$ from a source 85 to the inducing plate 83 produces a magnetic field that is parallel to the surface of the plate 83 and perpendicular to the direction of the current $I_d$ in the plate. This magnetic field in turn induces circulating eddy currents $I_e$ in the dish 3, that flow in one direction in the top half of the saline solution 5 and in the opposite direction in the lower half of the saline solution. Because of symmetry, there are no currents induced along the midline of the saline solution, and therefore it is necessary to have the dish depth equal to at least twice the thickness of the fillet 1, with the fillet 1 being located in either in the upper half or lower half of the dish. This would ensure that currents were induced throughout the fillet. The magnetometer 53 can be placed either on the side opposite the sheet inducer 83 or on the same side with the sheet inducer between the magnetometer and the dish, as the sheet inducer is very thin and does not appreciably increase the distance between the magnetometer and the fillet.

Figure 6:
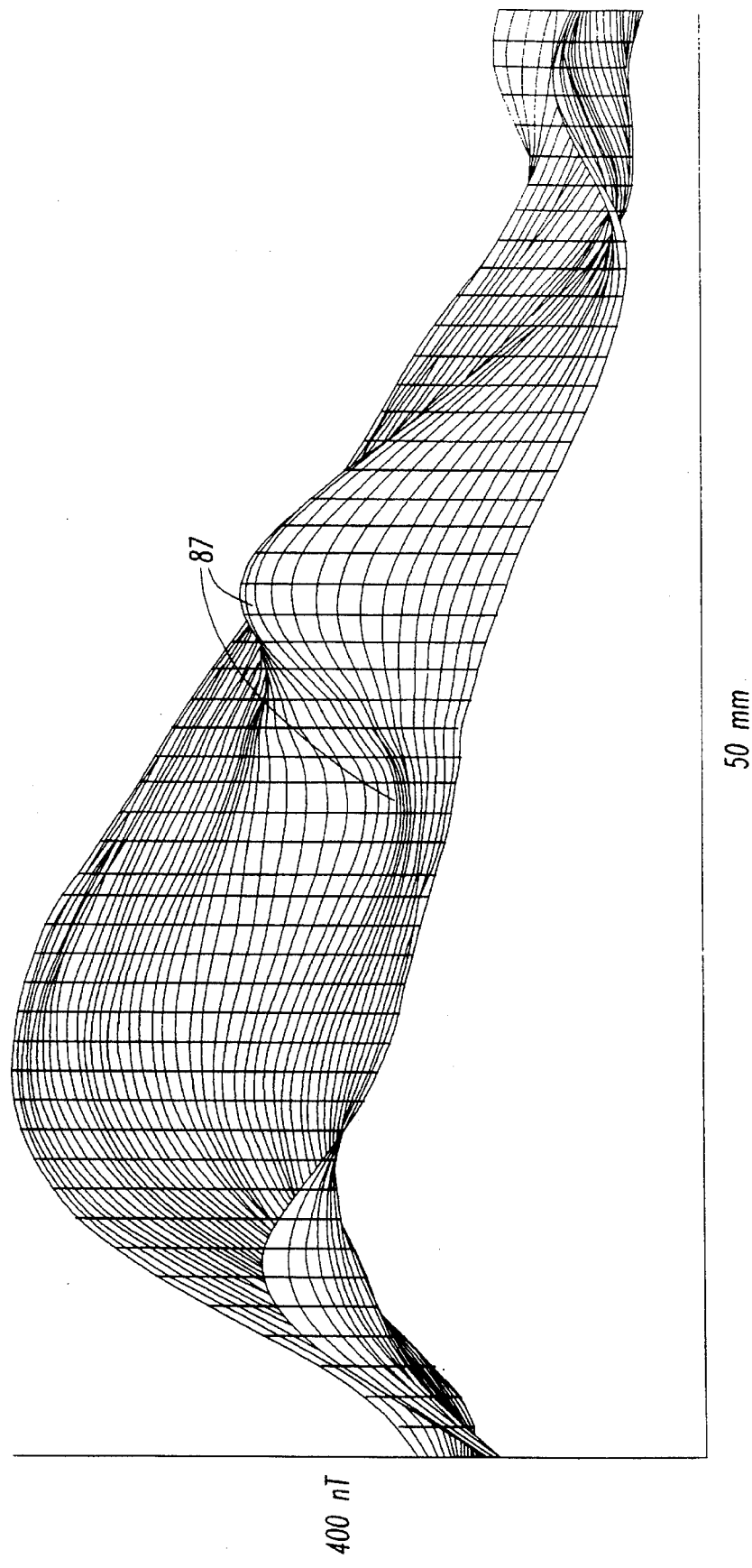
FIG. 6 is a surface plot of the magnetic field $B_z$ for the arrangement still another embodiment of the invention. of FIG. 2 when a dc current is applied.

FIG. 6 is a surface plot of the magnetic field, $B_z$, perpendicular to the fillet 1 for the configuration of FIG. 2 when a dc current is applied to the electrodes 35 and 37. The dipolar pattern 87 in the foreground is directly above the parasite 21. The surface plot of FIG. 6 has been rotated 90 degrees from the orientation of FIG. 2 to more clearly show the dipole. The current therefore flows away from the viewer. The area scanned by the SQUID magnetometer is 50 mm×50 mm. The z-scale runs from 0 to 400 nT.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed:

1. Apparatus for inspecting food products having a first electrical conductivity for inclusions having a second, substantially different electrical conductivity, said apparatus comprising:

a container containing a liquid electrolyte having an electrical conductivity substantially similar to said first electrical conductivity and in which said food products are immersed;

means producing an electrical current in said electrolyte which flows through said food products, said current producing a magnetic field;

detecting means for detecting a component of said magnetic field resulting from perturbations in said electric current produced by said inclusions; and means responsive to a predetermined magnitude of said component of said magnetic field to generate an output representative of the presence of said inclusion in said food product.

2. The apparatus of claim 1 wherein said container includes an inlet and an outlet and conveying means conveying a plurality of said food products serially through said container from said inlet to said outlet and past said detecting means while immersed in said electrolyte.

3. The apparatus of claim 2 wherein said container includes a center section disposed below and extending between said inlet and said outlet, said electrolyte being provided in said container to a level which maintains said center section completely filled with said electrolyte, said detecting means being located adjacent to said center section.

4. The apparatus of claim 3 wherein said means producing an electrical current in said electrolyte includes a coaxial cable having a center conductor and a coaxial conductor, a first electrode immersed in said electrolyte in said container adjacent to said inlet, a second electrode immersed in said electrolyte in said container adjacent to said outlet, and a cancelling conductor surrounding and extending along said center section of said container, said center conductor of said coaxial cable being connected to one of said first and second electrodes, and the coaxial conductor of said coaxial cable being connected to the other said first and second electrodes through said cancelling conductor.

5. The apparatus of claim 4 wherein said central section of said container has a longitudinal axis extending from adjacent said first electrode to adjacent said second electrode and said cancelling conductor is concentric with said longitudinal axis of said center portion of said container.

6. The apparatus of claim 3 wherein said means producing said electrical current in said electrolyte comprises an induction plate adjacent to said center section of said container and means applying an ac current to said induction plate.

7. The apparatus of claim 1 wherein said means producing said electrical current in said electrolyte comprises an induction plate adjacent said container, and means applying an ac current to said induction plate.

8. The apparatus of claim 1 wherein said means producing said electrical current in said electrolyte comprises a coaxial cable having a center conductor and a coaxial conductor, a first electrode immersed in said electrolyte adjacent a first end of said container, a second electrode immersed in said electrolyte adjacent a second end of said container, and a cancelling electrode surrounding said container between said first and second ends, said center conductor of said coaxial cable being connected to said first electrode and said coaxial conductor of said coaxial cable connected to said second electrode through said cancelling electrode.

9. The apparatus of claim 8 wherein said container has an axis extending between said first and second electrodes and said cancelling electrode is concentric with said container axis.

10. A method of inspecting food products having a first electrical conductivity for inclusions having a second, substantially different electrical conductivity, said method comprising the steps of:

immersing the food products in a liquid electrolyte having substantially said first electrical conductivity;

producing a distributed electrical current in said electrolyte which flows through said food products, said current producing a magnetic field; and detecting a component of said magnetic field resulting from perturbations in said distributed electrical current produced by said inclusions as an indication of the presence of said inclusion.

11. The method of claim 10 wherein the step of immersing comprises passing said food product through a bath of said electrolyte, and said step of detecting comprises detecting any perturbations in said magnetic field attributable to said inclusions as said food product passes through said bath of electrolyte.

12. The method of claim 11 wherein a plurality of said food products are passed serially through said bath of electrolyte, and said step of detecting comprises detecting any perturbations in said magnetic field for each of said plurality of food products.

13. The method of claim 10 wherein said electrolyte is contained within a container and said step of producing a distributed electrical current in the electrolyte comprises passing current through the electrolyte in said container in a first direction and then back around said container in an opposite direction.

14. The method of claim 10 wherein said step of producing a distributed electrical current in said electrolyte comprises inducing current in said electrolyte by generating a sheet of induction current adjacent to said electrolyte.

15. A method of inspecting food products having a first electrical conductivity when unspoiled, and a second, substantially different electrical conductivity when spoiled, said method comprising the steps of:

immersing the food product in a liquid electrolyte having substantially said first electrical conductivity, producing a distributed electrical current in said electrolyte which flows through said food product, said distributed electrical current producing a magnetic field, and detecting a component of said magnetic field resulting from perturbations in said distributed electrical current perpendicular to said distributed electrical current at a boundary between said food product and said electrolyte when said food product is spoiled and has said second electrical conductivity as an indication of said food product being spoiled.

16. The method of claim 15 wherein said step of immersing comprises passing said food product through a bath of said electrolyte and said detecting comprises detecting said perturbations in said magnetic field as said food product passes through said bath of electrolyte.

17. The method of claim 16 wherein a plurality of said food products are passed serially through said bath of electrolyte, and said step of detecting comprises selecting any perturbations in said magnetic field for each of said plurality of food products.

* * * * *

UNITED STATES PATENT AND TRADEMARK OFFICE
CERTIFICATE OF CORRECTION

PATENT NO. : 5,572,123

DATED : November 5, 1996

INVENTOR(S) : John P. Wikswo, Jr., et al.

It is certified that error appears in the above-identified patent and that said Letters Patent is hereby corrected as shown below:

Column 1, line 7, "NA66D0046" should be -- NA66FD0046 --.

Column 1, lines 31, 35, 39, 46, "canalling" should be -- candling --.

Column 3, line 24, -- still another embodiment of the invention. -- should be inserted after "representation of".

Claim 17, column 8, line 62, "selecting" should be -- detecting --.

Signed and Sealed this

Ninth Day of December, 1997

Attest:

BRUCE LEHMAN

Attesting Officer

Commissioner of Patents and Trademarks